United States Patent
Shelton, IV et al.

(10) Patent No.: US 7,487,899 B2
(45) Date of Patent: Feb. 10, 2009

(54) SURGICAL INSTRUMENT INCORPORATING EAP COMPLETE FIRING SYSTEM LOCKOUT MECHANISM

(75) Inventors: Frederick E. Shelton, IV, Hillsboro, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 116 days.

(21) Appl. No.: 11/096,096

(22) Filed: Mar. 31, 2005

(65) Prior Publication Data

US 2006/0022014 A1 Feb. 2, 2006

Related U.S. Application Data

(60) Provisional application No. 60/591,694, filed on Jul. 28, 2004.

(51) Int. Cl.
*A61B 17/068* (2006.01)
(52) U.S. Cl. .............. 227/175.1; 227/175.3; 227/175.4; 227/176.1; 227/19
(58) Field of Classification Search .............. 227/175.2, 227/175.3, 175.4, 176.1, 19
See application file for complete search history.

(56) References Cited

U.S. PATENT DOCUMENTS

| | | | |
|---|---|---|---|
| 2,711,461 A | 6/1965 | Happe | |
| 5,031,814 A | 7/1991 | Tompkins et al. | |
| 5,071,052 A | 12/1991 | Rodak et al. | |
| 5,137,198 A | 8/1992 | Nobis et al. | |
| 5,171,249 A | 12/1992 | Stefanchik et al. | |
| 5,202,914 A | 4/1993 | Kim et al. | |
| 5,263,629 A | 11/1993 | Trumbull et al. | |
| 5,290,240 A | 3/1994 | Horres | |
| 5,372,124 A | 12/1994 | Takayama et al. | |
| 5,387,194 A | 2/1995 | Williams | |
| 5,389,098 A | 2/1995 | Tsuruta et al. | |

(Continued)

FOREIGN PATENT DOCUMENTS

EP 0741966 11/1996

(Continued)

OTHER PUBLICATIONS

EPO Search Report, Application No. 05254680.1, Jan. 12, 2006, pp. 1-5.

(Continued)

*Primary Examiner*—Rinaldi I. Rada
*Assistant Examiner*—Nathaniel Chukwurah
(74) *Attorney, Agent, or Firm*—Frost Brown Todd LLC

(57) ABSTRACT

A surgical stapling and severing instrument particularly suited to endoscopic procedures incorporates a handle that produces separate closing and firing motions to actuate an end effector. In particular, the handle produces multiple firing strokes in order to reduce the required amount of force required to fire (i.e., staple and sever) the end effector. A linked transmission reduces the required handle longitudinal length, yet achieves a rigid, strong configuration when straightened for firing. A spring-biased side pawl firing mechanism is enabled by activation of an Electroactive Polymer (EAP) block actuator that overcomes a disengagement spring bias and moves a linked rack into proximity with a side pawl firing mechanism. Thereby, various sensed or commanded inputs may be incorporated to prevent inadvertent firing.

21 Claims, 12 Drawing Sheets

U.S. PATENT DOCUMENTS

| | | |
|---|---|---|
| 5,397,046 A | 3/1995 | Savage et al. |
| 5,397,324 A | 3/1995 | Carroll et al. |
| 5,403,312 A | 4/1995 | Yates et al. |
| 5,413,267 A | 5/1995 | Solyntjes et al. |
| 5,413,268 A | 5/1995 | Green et al. |
| 5,431,668 A | 7/1995 | Burbank, III et al. |
| 5,441,193 A | 8/1995 | Gravener |
| 5,445,304 A | 8/1995 | Plyley et al. |
| 5,465,895 A | 11/1995 | Knodel et al. |
| 5,484,095 A | 1/1996 | Green et al. |
| 5,503,638 A | 4/1996 | Cooper et al. |
| 5,535,937 A | 7/1996 | Boiarski et al. |
| 5,542,594 A | 8/1996 | McKean et al. |
| 5,549,628 A | 8/1996 | Cooper et al. |
| 5,562,239 A | 10/1996 | Boiarski et al. |
| 5,584,425 A | 12/1996 | Savage et al. |
| 5,599,329 A | 2/1997 | Gabbey |
| 5,601,582 A | 2/1997 | Shelton et al. |
| 5,602,914 A | 2/1997 | Andreini |
| 5,624,452 A | 4/1997 | Yates |
| 5,634,584 A | 6/1997 | Okorocha et al. |
| 5,653,721 A * | 8/1997 | Knodel et al. ............... 606/151 |
| 5,661,887 A | 9/1997 | Byrne |
| 5,665,285 A | 9/1997 | Hattori et al. |
| 5,667,517 A * | 9/1997 | Hooven ...................... 606/151 |
| 5,673,840 A | 10/1997 | Schulze et al. |
| 5,673,841 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze |
| 5,693,042 A * | 12/1997 | Boiarski et al. ............... 606/10 |
| 5,702,409 A | 12/1997 | Rayburn et al. |
| 5,709,334 A | 1/1998 | Sorrentino et al. |
| 5,735,445 A | 4/1998 | Vidal et al. |
| 5,769,892 A | 6/1998 | Kingwell |
| 5,779,130 A | 7/1998 | Alesi et al. |
| 5,797,537 A | 8/1998 | Oberlin et al. |
| 5,810,855 A | 9/1998 | Rayburn et al. |
| 5,826,776 A | 10/1998 | Schulze et al. |
| 5,829,662 A | 11/1998 | Allen et al. |
| 5,855,565 A | 1/1999 | Bar-Cohen |
| 5,865,361 A | 2/1999 | Milliman et al. |
| 5,876,401 A | 3/1999 | Schulze et al. |
| 5,901,895 A | 5/1999 | Heaton et al. |
| 5,902,312 A | 5/1999 | Frater et al. |
| 5,908,427 A | 6/1999 | McKean et al. |
| 5,918,791 A | 7/1999 | Sorrentino et al. |
| 5,959,852 A * | 9/1999 | Deloy et al. .................. 363/45 |
| 5,964,774 A | 10/1999 | McKean et al. |
| 6,010,054 A | 1/2000 | Johnson et al. |
| 6,032,849 A * | 3/2000 | Mastri et al. ............... 227/176.1 |
| 6,063,097 A | 5/2000 | Oi et al. |
| 6,079,606 A | 6/2000 | Milliman et al. |
| 6,109,500 A * | 8/2000 | Alli et al. ................. 227/175.2 |
| 6,202,914 B1 | 3/2001 | Geiste et al. |
| 6,302,311 B1 | 10/2001 | Adams et al. |
| 6,330,965 B1 | 12/2001 | Milliman |
| 6,503,257 B2 | 1/2003 | Grant et al. |
| 6,503,259 B2 | 1/2003 | Huxel |
| 6,577,899 B2 | 6/2003 | Lebel et al. |
| 6,586,859 B2 | 7/2003 | Kornbluh et al. |
| 6,652,521 B2 | 11/2003 | Schulze |
| 6,656,193 B2 | 12/2003 | Grant et al. |
| 6,667,825 B2 | 12/2003 | Lu et al. |
| 6,669,073 B2 | 12/2003 | Milliman |
| 6,716,233 B1 | 4/2004 | Whitman |
| 6,740,079 B1 | 5/2004 | Eggers |
| 6,786,382 B1 | 9/2004 | Hoffman |
| 6,830,174 B2 | 12/2004 | Hillstead |
| 6,835,173 B2 | 12/2004 | Couvillon, Jr. |
| 6,840,246 B2 | 1/2005 | Downing |
| 6,905,057 B2 * | 6/2005 | Swayze et al. ............ 227/176.1 |
| 6,923,804 B2 | 8/2005 | Eggers et al. |
| 6,959,852 B2 * | 11/2005 | Shelton et al. ............ 227/182.1 |
| 6,964,363 B2 | 11/2005 | Wales et al. |
| 6,969,395 B2 | 11/2005 | Esuri |
| 6,978,921 B2 | 12/2005 | Shelton |
| 6,981,628 B2 | 1/2006 | Shelton |
| 6,988,649 B2 | 1/2006 | Shelton |
| 7,000,818 B2 | 2/2006 | Shelton |
| 7,000,819 B2 * | 2/2006 | Swayze et al. ............ 227/176.1 |
| 7,044,352 B2 | 5/2006 | Shelton, IV et al. |
| 7,055,731 B2 | 6/2006 | Shelton |
| 7,063,699 B2 | 6/2006 | Hess et al. |
| 7,074,217 B2 | 7/2006 | Strul et al. |
| 7,083,075 B2 | 8/2006 | Swayze |
| 7,111,769 B2 | 9/2006 | Wales. |
| 7,140,528 B2 | 11/2006 | Shelton |
| 7,143,925 B2 | 12/2006 | Shelton |
| 7,143,926 B2 | 12/2006 | Shelton |
| 7,147,138 B2 | 12/2006 | Shelton |
| 7,208,005 B2 | 4/2007 | Frecker |
| 7,213,736 B2 | 5/2007 | Wales et al. |
| 7,364,061 B2 | 4/2008 | Swayze et al. |
| 7,367,485 B2 | 5/2008 | Shelton, IV et al. |
| 7,380,696 B2 | 6/2008 | Shelton, IV et al. |
| 2001/0029384 A1 | 10/2001 | Nicholas et al. |
| 2002/0074005 A1 | 6/2002 | Hobb et al. |
| 2002/0165541 A1 | 11/2002 | Whitman |
| 2003/0065358 A1 | 4/2003 | Frecher |
| 2003/0069474 A1 | 4/2003 | Couvillion et al. |
| 2003/0199870 A1 | 10/2003 | Truckal et al. |
| 2003/0236531 A1 | 12/2003 | Couvillon, Jr. |
| 2004/0002726 A1 | 1/2004 | Nunez et al. |
| 2004/0050971 A1 | 3/2004 | Rueger |
| 2004/0097971 A1 | 5/2004 | Hughett |
| 2004/0149802 A1 | 8/2004 | Whitman |
| 2004/0232195 A1 * | 11/2004 | Shelton et al. ............ 227/175.1 |
| 2004/0232196 A1 | 11/2004 | Shelton et al. |
| 2004/0232197 A1 | 11/2004 | Shelton et al. |
| 2005/0006431 A1 | 1/2005 | Shelton et al. |
| 2005/0006434 A1 | 1/2005 | Wales et al. |
| 2005/0067457 A1 | 3/2005 | Shelton et al. |
| 2005/0067458 A1 | 3/2005 | Swayze et al. |
| 2005/0085693 A1 | 4/2005 | Belson et al. |
| 2005/0165415 A1 | 7/2005 | Wales |
| 2005/0173490 A1 * | 8/2005 | Shelton .................... 227/175.2 |
| 2006/0016853 A1 | 1/2006 | Racenet |
| 2006/0022014 A1 | 2/2006 | Shelton et al. |
| 2006/0022015 A1 * | 2/2006 | Shelton et al. ............ 227/176.1 |
| 2006/0025809 A1 | 2/2006 | Shelton |
| 2006/0025810 A1 | 2/2006 | Shelton, IV |
| 2006/0025811 A1 | 2/2006 | Shelton, IV |
| 2006/0025812 A1 * | 2/2006 | Shelton .................... 606/205 |
| 2006/0025813 A1 | 2/2006 | Shelton, IV et al. |
| 2006/0025816 A1 * | 2/2006 | Shelton .................... 606/215 |
| 2006/0025817 A1 | 2/2006 | Ortiz |
| 2006/0041273 A1 | 2/2006 | Ortiz |
| 2006/0047302 A1 | 3/2006 | Ortiz |
| 2006/0047303 A1 | 3/2006 | Ortiz |
| 2006/0047305 A1 | 3/2006 | Ortiz |
| 2006/0047306 A1 | 3/2006 | Ortiz |
| 2006/0047307 A1 | 3/2006 | Ortiz |
| 2006/0047308 A1 | 3/2006 | Ortiz |
| 2006/0060630 A1 * | 3/2006 | Shelton et al. ............ 227/175.2 |
| 2006/0190028 A1 | 8/2006 | Wales et al. |
| 2006/0212069 A1 | 9/2006 | Shelton, IV |

FOREIGN PATENT DOCUMENTS

| | | |
|---|---|---|
| EP | 0 832 605 | 4/1998 |
| EP | 1 522 264 | 4/2005 |
| WO | WO 99/02090 | 1/1999 |
| WO | WO 00/78222 | 12/2000 |

| | | |
|---|---|---|
| WO | WO 01/62158 | 8/2001 |
| WO | WO 01/62163 | 8/2001 |
| WO | WO 03/088845 | 10/2003 |
| WO | WO 03/090630 | 11/2003 |
| WO | WO 03/094743 | 11/2003 |
| WO | WO 2004/014238 | 2/2004 |
| WO | WO 2004/050971 | 6/2004 |

OTHER PUBLICATIONS

EPO Search Report, Application No. 05254694.2, Jan. 12, 2006, pp. 1-5.
EPO Search Report, Application No. 05254685.0, Jan. 12, 2006, pp. 1-5.
EPO Search Report, Application No. 05254695.9, Jan. 12, 2006, pp. 1-5.
EPO Search Report, Application No. 06255058.7, Jan. 31, 2007, pp. 1-3.
Notice of Allowance for U.S. Appl. No. 11/066,371 dated Jul. 25, 2006.
Notice of Allowance for U.S. Appl. No. 11/082,495, dated Sep. 19, 2007.
Notice of Allowance for U.S. Appl. No. 11/083,740 dated Sep. 25, 2006.
Notice of Allowance for U.S. Appl. No. 11/096,158 dated May 23, 2006.
Notice of Allowance for U.S. Appl. No. 11/157,767 dated Aug. 14, 2006.
Notice of Allowance for U.S. Appl. No. 11/181,471 dated Aug. 22, 2006.
Notice of Allowance for U.S. Appl. No. 11/240,836, dated Sep. 12, 2007.
Office Action dated Nov. 13, 2006 for U.S. Appl. No. 11/181,046.
Office Action dated Mar. 22, 2007 for U.S. Appl. No. 11/082,495.
Office Action dated Aug. 29, 2007 for U.S. Appl. No. 11/181,046.
U.S. Appl. No. 10/441,362, filed May 20, 2003, Ho.
U.S. Appl. No. 10/441,424, filed May 20, 2003, Shelton, IV et al.
U.S. Appl. No. 10/615,971, filed Jul. 9, 2003, Wales et al.
U.S. Appl. No. 10/615,973, filed Jul. 9, 2003, Wales et al.
U.S. Appl. No. 10/673,929, filed May 9, 2003, Shelton, IV et al.
U.S. Appl. No. 11/052,387, filed Feb. 7, 2005, Shelton, IV et al.
U.S. Appl. No. 11/052,632, filed Feb. 7, 2005, Rao et al.
U.S. Appl. No. 11/082,495, filed Mar. 17, 2005, Shelton, IV.
U.S. Appl. No. 11/083,740, filed Mar. 18, 2005, Wales et al.
U.S. Appl. No. 11/162,984, filed Sep. 3, 2005, Ortiz et al.
U.S. Appl. No. 11/162,985, filed Sep. 30, 2005, Ortiz et al.
U.S. Appl. No. 11/162,986, filed Sep. 30, 2005, Ortiz et al.
U.S. Appl. No. 11/162,988, filed Sep. 30, 2005, Ortiz et al.
U.S. Appl. No. 11/162,989, filed Sep. 30, 2005, Ortiz et al.
U.S. Appl. No. 11/162,990, filed Sep. 30, 2005, Ortiz et al.
U.S. Appl. No. 11/162,991, filed Sep. 30, 2005, Ortiz et al.
U.S. Appl. No. 11/162,992, filed Sep. 30, 2005, Ortiz et al.
U.S. Appl. No. 11/240,836, filed Sep. 30, 2005, Shelton, IV et al.
U.S. Appl. No. 60/591,694, filed Jul. 28, 2004, Shelton, IV.
Non-Final Rejection dated Aug. 7, 2007 for U.S. Appl. No. 11/162,990.
Non-Final Rejection dated Sep. 21, 2007 for U.S. Appl. No. 11/162,986.
Non-Final Rejection dated Sep. 21, 2007 for U.S. Appl. No. 11/162,988.
Notice of Allowance dated Dec. 1, 2006 for U.S. Appl. No. 10/955,042.
Notice of Allowance dated Oct. 1, 2007 for U.S. Appl. No. 10/955,042.
Notice of Allowance dated Mar. 13, 2008 for U.S. Appl. No. 11/240,836.
Office Action dated Mar. 15, 2006 for U.S. Appl. No. 10/955,042.
Office Action dated Mar. 22, 2007 for U.S. Appl. No. 11/082,495.
Notice of Allowance dated Mar. 29, 2007 for U.S. Appl. No. 10/955,042.
Examination Report for Application 05254680, Sep. 22, 2006.
Examination Report for Application 05254685, Sep. 22, 2006.
Examination Report for Application 05254694, Sep. 22, 2006.
Examination Report for Application 05254695, Sep. 22, 2006.
Guidelines for Hand and Power Tools, http://www.osha.gov/doc/outreachtraining/htmlfiles/tools.html, OSHA, May 1996, p. 3.
Final Rejection dated Oct. 18, 2006 for U.S. Appl. No. 11/096,096.
Non-Final Rejection dated Nov. 13, 2006 for U.S. Appl. No. 11/181,046.
Non-Final Rejection dated Aug. 7, 2007 for U.S. Appl. No. 11/162,990.
Non-Final Rejection dated Aug. 29, 2007 for U.S. Appl. No. 11/181,046.
Non-Final Rejection dated Sep. 21, 2007 for U.S. Appl. No. 11/162,986.
Non-Final Rejection dated Sep. 21, 2007 for U.S. Appl. No. 11/162,988.
Non-Final Rejection dated May 5, 2008 for U.S. Appl. No. 11/181,046.
Office Action dated Mar. 15, 2006 for U.S. Appl. No. 10/955,042.
Office Action dated Mar. 22, 2007 for U.S. Appl. No. 11/082,495.
Office Action dated Mar. 29, 2007 for U.S. Appl. No. 10/955,042.
Notice of Allowance dated Mar. 23, 2006 for U.S. Appl. No. 11/096,158.
Notice of Allowance dated Jul. 25, 2006 for U.S. Appl. No. 11/066,371.
Notice of Allowance dated Aug. 14, 2006 for U.S. Appl. No. 11/157,767.
Notice of Allowance dated Aug. 22, 2006 for U.S. Appl. No. 11/181,471.
Notice of Allowance dated Sep. 25, 2006 for U.S. Appl. No. 11/083,470.
Notice of Allowance dated Dec. 1, 2006 for U.S. Appl. No. 10/955,042.
Notice of Allowance dated Sep. 12, 2007 for U.S. Appl. No. 11/240,836.
Notice of Allowance dated Sep. 19, 2007 for U.S. Appl. No. 11/082,495.
Notice of Allowance dated Oct. 1, 2007 for U.S. Appl. No. 10/955,042.
Notice of Allowance dated Mar. 13, 2006 for U.S. Appl. No. 11/240,836.
Notice of Allowance dated Apr. 10, 2008 for U.S. Appl. No. 11/082,495.
Notice of Allowance dated Apr. 10, 2008 for U.S. Appl. No. 11/162,990.
Notice of Allowance dated Apr. 18, 2008 for U.S. Appl. No. 11/162,985.
Notice of Allowance dated Apr. 18, 2008 for U.S. Appl. No. 11/162,986.
Notice of Allowance dated Apr. 18, 2008 for U.S. Appl. No. 11/162,988.
Notice of Allowance dated Jun. 10, 2008 for U.S. Appl. No. 11/082,495.
Notice of Allowance dated Jun. 10, 2008 for U.S. Appl. No. 11/240,836.
Notice of Allowance dated Aug. 11, 2008 for U.S. Appl. No. 11/082,495.
EPO Search Report dated Sep. 22, 2006 for Application No. 05254680.
EPO Search Report dated Feb. 29, 2008 for Application No. 05254681.9.
EPO Search Report dated Sep. 22, 2006 for Application No. 05254685.
EPO Search Report dated Sep. 22, 2006 for Application No. 05254694.
EPO Search Report dated Sep. 22, 2006 for Application No. 05254695.
EPO Search Report dated Mar. 3, 2008 for Application No. 05254699.1.
EPO Search Report dated Feb. 26, 2008 for Application No. 05254700.7.
EPO Search Report dated Mar. 25, 2008 for Application No. 05254703.1.

* cited by examiner

SURGICAL INSTRUMENT INCORPORATING EAP COMPLETE FIRING SYSTEM LOCKOUT MECHANISM

CROSS REFERENCE TO RELATED APPLICATIONS

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

The present application claims the benefit of commonly-owned U.S. patent application Ser. No. 11/052,387 filed on 7 Feb. 2005 and entitled "SURGICAL STAPLING INSTRUMENT INCORPORATING A MULTI-STROKE FIRING MECHANISM WITH RETURN SPRING ROTARY MANUAL RETRACTION SYSTEM", the disclosure of which is hereby incorporated by reference in its entirety.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that preclude inadvertent firing.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Generally, a single closing stroke followed by a single firing stroke is a convenient and efficient way to perform severing and stapling. However, in some instances, multiple firing strokes are desirable. For example, surgeons select a length of staple cartridge for the desired length of cut from a range of jaw sizes. Longer staple cartridges require a longer firing stroke. Thus, to effect the firing, a hand-squeezed trigger is required to exert a larger force for these longer staple cartridges in order to sever more tissue and drive more staples as compared to a shorter staple cartridge. It would be desirable for the amount of force to be lower and comparable to shorter cartridges so as not to exceed the hand strength of some surgeons. In addition, some surgeons, not familiar with the larger staple cartridges, may become concerned that binding or other malfunction has occurred when an unexpectedly higher force is required.

In U.S. patent application Ser. No. 11/066,371 entitled "SURGICAL STAPLING INSTRUMENT HAVING AN ELECTROACTIVE POLYMER ACTUATED SINGLE LOCKOUT MECHANISM FOR PREVENTION OF FIRING" to Shelton filed 25 Feb. 2005, the disclosure of which is hereby incorporated by reference in its entirety, an EAP lockout actuator is advantageously incorporated into an implement portion to block a firing member to prevent firing. Thereby, an undesirable situation is avoided such as when full or partial firing occurs, causing severing of clamped tissue, without the surgical instrument being capable of forming staples.

While such an EAP lockout mechanism incorporated into the implement portion has certain advantages, it is desirable in some instances to provide an alternative or an additional lockout mechanism.

Consequently, a significant need exists for an improved surgical stapling and severing instrument that prevents inadvertent firing (i.e., severing and stapling) when a either the instrument or the surgeon are not prepared to fully sever and staple clamped tissue.

BRIEF SUMMARY OF THE INVENTION

The invention overcomes the above-noted and other deficiencies of the prior art by providing a surgical stapling and severing instrument that advantageously incorporates a multiple firing stroke handle that actuates a long end effector without undue manual force required by the surgeon. Yet, depression of the multiple firing stroke handle is precluded from imparting a firing force into a firing mechanism until conditions allow electrically overcoming a disengaging bias.

In one aspect of the invention, a surgical instrument includes an implement portion that is actuated by a reciprocating firing actuator engaging a distally moving, proximal engaging portion of a firing member. In particular, an engagement mechanism selectively couples the proximate and aligned the firing actuator and the firing member for movement when a lockout mechanism allows engagement. To that end, the lockout mechanism has a disengaging biasing member uncoupling the engagement mechanism except when an electrical actuator, which is opposingly positioned, overcomes the disengaging biasing member. Thereby, a firing mechanism defaults to be disengaged, with a surgeon allows to depress a firing actuator, such as a trigger, without firing being effected. Thus, inadvertent depression of the firing member or depression when the instrument is not ready to properly fire, does not actually result in firing.

In another aspect of the invention, a surgical instrument has an end effector with pivotally attached opposing jaws and a staple cartridge contained in one of the opposing jaws for stapling and severing tissue. A firing bar actuates the end effector to effect stapling and severing of clamped tissue. A rack is proximally attached to the firing bar and is distally translated by a reciprocating firing actuator proximate to and aligned with the rack when coupled together by an engagement mechanism. A lockout mechanism advantageously prevents this engagement for firing as a default by a disengaging biasing member uncoupling the engagement mechanism from the rack until an electrical actuator opposingly positioned overcomes the disengaging biasing member when activated. There inadvertent severing of tissues or premature ejection of staples is avoided.

In yet another aspect of the invention, a surgical instrument has a firing bar that translates within an elongate shaft to cause an end effector attached distally thereto to perform a surgical operation. A rack proximally coupled to the firing bar is encompassed and guided by a handle. A firing trigger is also attached for movement to the handle to drive a pawl into engagement with the rack during distal movement thereof to effect firing except when an electroactive polymer actuator is not urging the pawl toward engagement with the rack.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
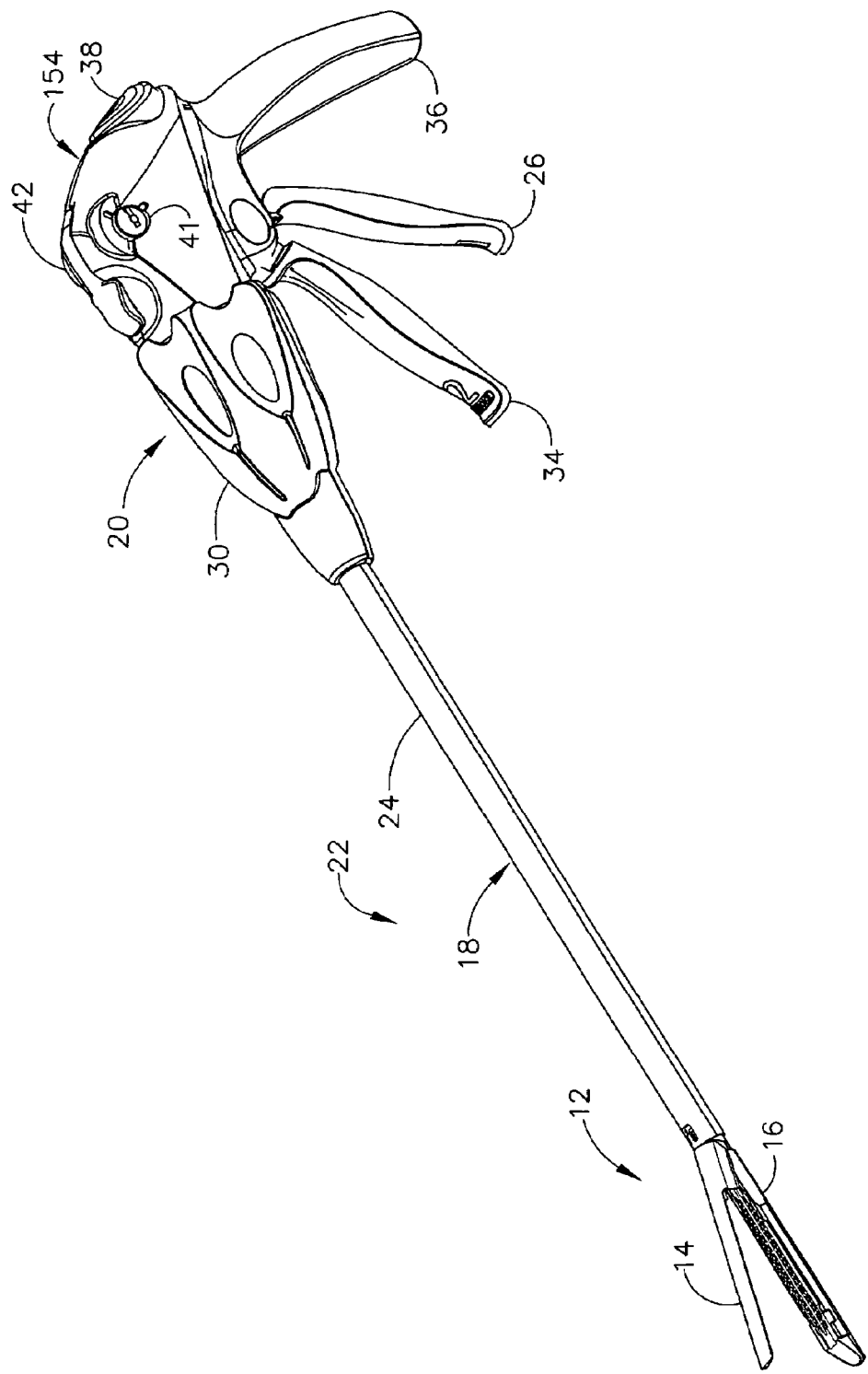
FIG. 1 is a left front perspective view of a surgical stapling and severing instrument incorporating an Electroactive Polymer (EAP) blocking, complete lockout mechanism in a handle portion.
Figure 2:
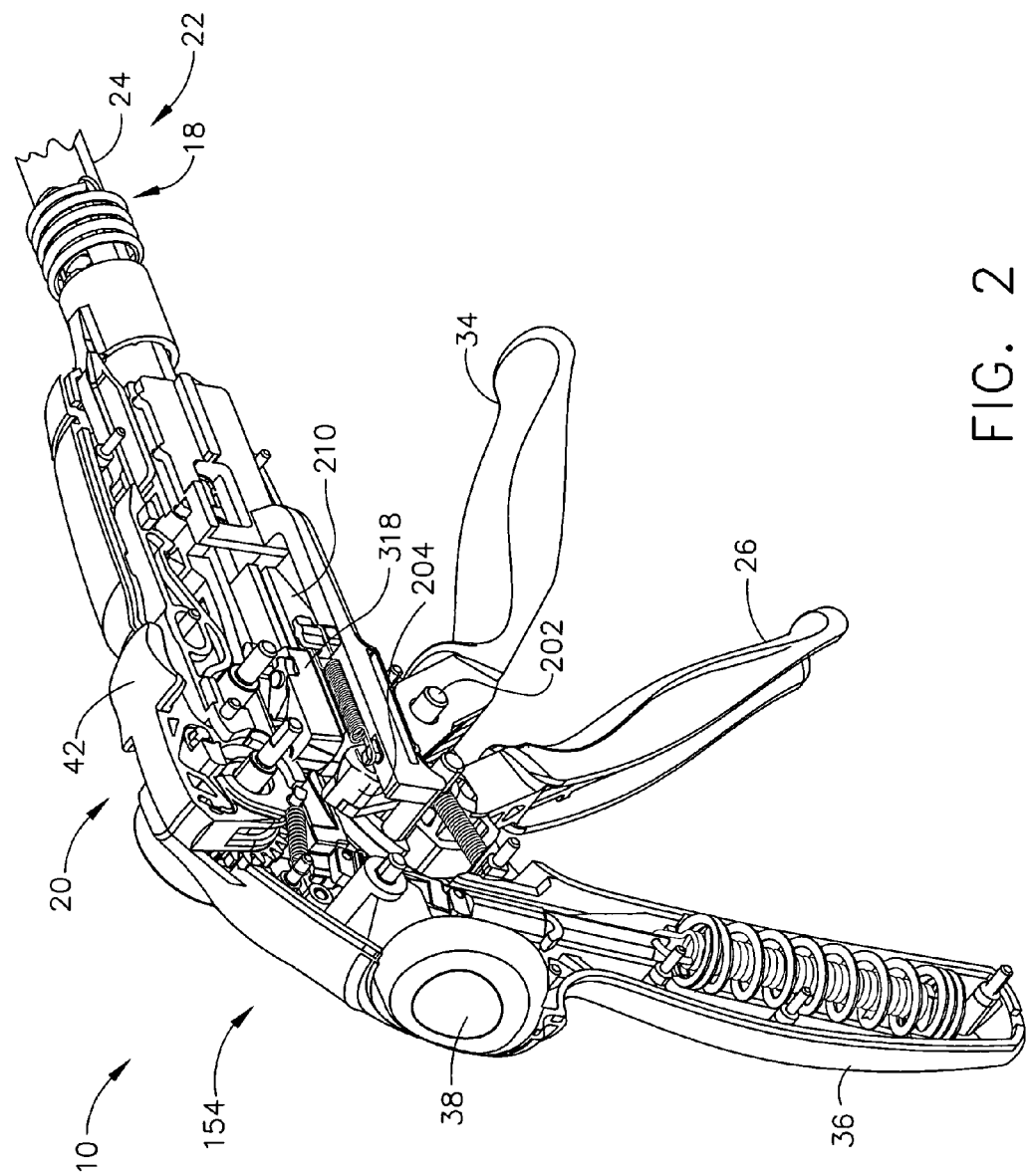
FIG. 2 is a right aft perspective view of the handle portion of the surgical stapling and severing instrument of FIG. 1 with a right half shell of a handle housing removed to expose closure and firing mechanisms.

In FIG. 1, a surgical stapling and severing instrument 10 includes multi-stroke firing of an end effector, which in the illustrative version is a staple applying assembly 12. An anvil 14 may be repeatably opened and closed about its pivotal attachment to an elongate (staple) channel 16. The staple applying assembly 12 is proximally attached to elongate shaft 18, forming an implement portion 22. When the staple applying assembly 12 is closed, the implement portion 22 presents a small cross-sectional area suitable for insertion through a trocar by an externally connected and manipulating handle 20.

The handle 20 has user controls mounted on its handle housing 154 user controls such as a rotation knob 30 that rotates the elongate shaft 18 and staple applying assembly 12 about a longitudinal axis of the shaft 18. A closure trigger 26, which pivots in front of a pistol grip 36 about a closure trigger pin 152 engaged laterally across the handle housing 154, is depressed to close the staple applying assembly 12. A multiple stroke firing trigger 34, which pivots in front of the closure trigger 26, causes the staple applying assembly 12 to simultaneously sever and staple tissue clamped therein. Since multiple firing strokes are employed to reduce the amount of force required per stroke by the surgeon's hand, right and left indicator wheels 40, 41 (the latter depicted in FIG. 3) rotate presenting indicia of the firing progress. For instance, full firing travel may require three full firing strokes and thus the indicator wheels 40, 41 rotate up to one-third of a revolution each per stroke. A manual firing release lever 42 allows retraction before full firing travel if desired and allows assistance to retract in the presence of binding or a failure in the retraction bias. A closure release button 38 is outwardly presented when the closure trigger 26 is clamped and partial firing has not occurred that would prevent unclamping the closure trigger 26.

Figure 3:
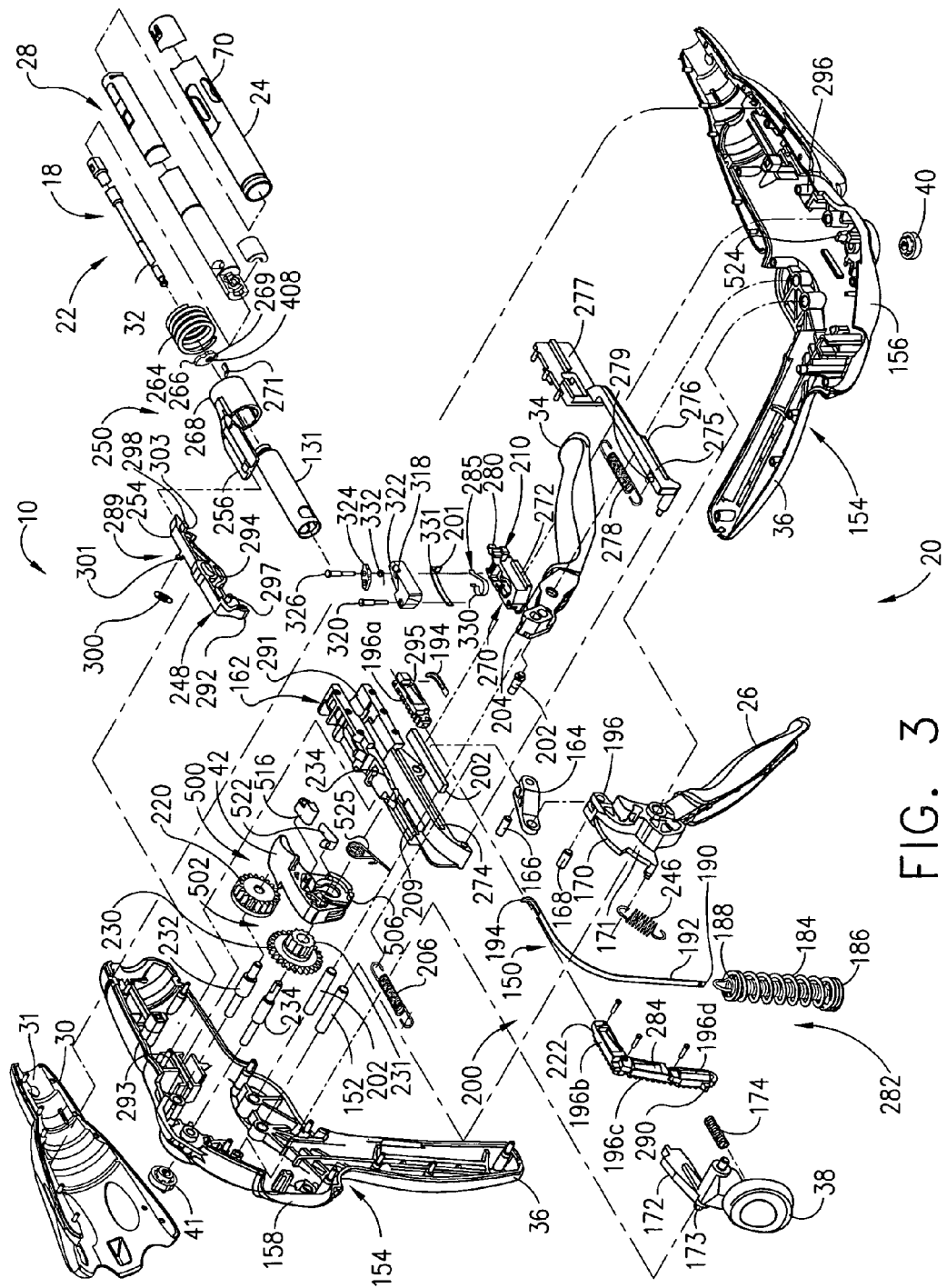
FIG. 3 is a right aft perspective disassembled view of the handle portion and an elongate shaft of the surgical stapling and severing instrument of FIG. 1.

With reference to FIGS. 1-5, the elongate shaft 18 has as its outer structure a longitudinally reciprocating closure tube 24 that pivots the anvil 14 to effect closure in response to proximal depression of the closure trigger 26 of the handle 20. With particular reference to FIG. 3, the elongate channel 18 is connected to the handle 20 by a frame 28 that is internal to the closure tube 24. The frame 28 is rotatably engaged to the handle 20 so that twisting the rotation knob 30 causes rotation of the implement portion 22. With particular reference to FIG. 3, each half shell of the rotation knob 30 includes an inward projection 31 that enters a respective longer side opening 70 in the closure tube 24 and moves inward to engage the frame 28 that determines the rotated position of the implement portion 22. The longitudinal length of the longer opening 70 is sufficiently long to allow longitudinal closure motion of the closure tube 24.

An upper portion 160 of the closure trigger 26 pushes forward a closure yoke 162 via a closure link 164. The closure link 164 is pivotally attached at its distal end by a closure yoke pin 166 to the closure yoke 162 and is pivotally attached at its proximal end by a closure link pin 168. The closure trigger 26 is urged to the open position by a closure trigger tension spring 246 that is connected proximally to the upper portion 160 of the closure trigger 26 and to a handle housing 154 formed by right and left half shells 156, 158.

The upper portion 160 of the closure trigger 26 includes a proximal crest 170 with an aft notch 171. The closure release button 38 and a pivoting locking arm 172 are connected by a central lateral pivot 173. A compression spring 174 biases the closure release button 38 proximally (clockwise about the central lateral pivot 173 as viewed from the right), With the upper portion 160 back when the closure trigger 26 is released as depicted in FIGS. 34-35, the pivoting locking arm 172 rides upon the proximal crest 170 drawing in the closure release button 38. When the closure trigger 26 reaches its fully depressed position, it should be appreciated that the aft notch 171 is presented below the pivoting locking arm 172, which drops into and locks against the aft notch 171 under the urging of the compression spring 174. With the firing components retracted, manual depression of the closure release button 38 rotates the pivoting locking arm 172 upward unclamping the closure trigger 26.

Once the closure trigger 26 is proximally clamped, a firing rod 32 is distally moved from the handle 20 in response to the multiple stroke firing trigger 34 being drawn to the pistol grip 36 with the amount of firing travel visible to the surgeon on right and left indicator gauge wheels 40, 41. The firing trigger 34 pivots about a firing trigger pin 202 that laterally traverses and is engaged to the right and left half shells 156, 158.

A linked transmission firing mechanism 150 is initially retracted, urged to remain in this position by the combination tension/compression spring 184 that is constrained within the pistol grip 36 of the handle 20, with its nonmoving end 186 connected to a housing 154 and a moving end 188 connected to a downwardly flexed and proximal, retracted end 190 of a steel band 192.

A distally-disposed end 194 of the steel band 192 is attached to an attachment feature 195 on a front link 196a of a plurality of links 196a-1196d that form a linked rack 200. Linked rack 200 is flexible yet has distal links that form a straight rigid rack assembly that may transfer a significant firing force through the firing rod 32 in the implement portion 22, yet readily retracts into the pistol grip 36 to minimize the longitudinal length of the handle 20. It should be appreciated that the combination tension/compression spring 184 increases the amount of firing travel available while essentially reducing the minimum length by half over a single spring.

Anti-Backup Mechanism.

Figure 4:
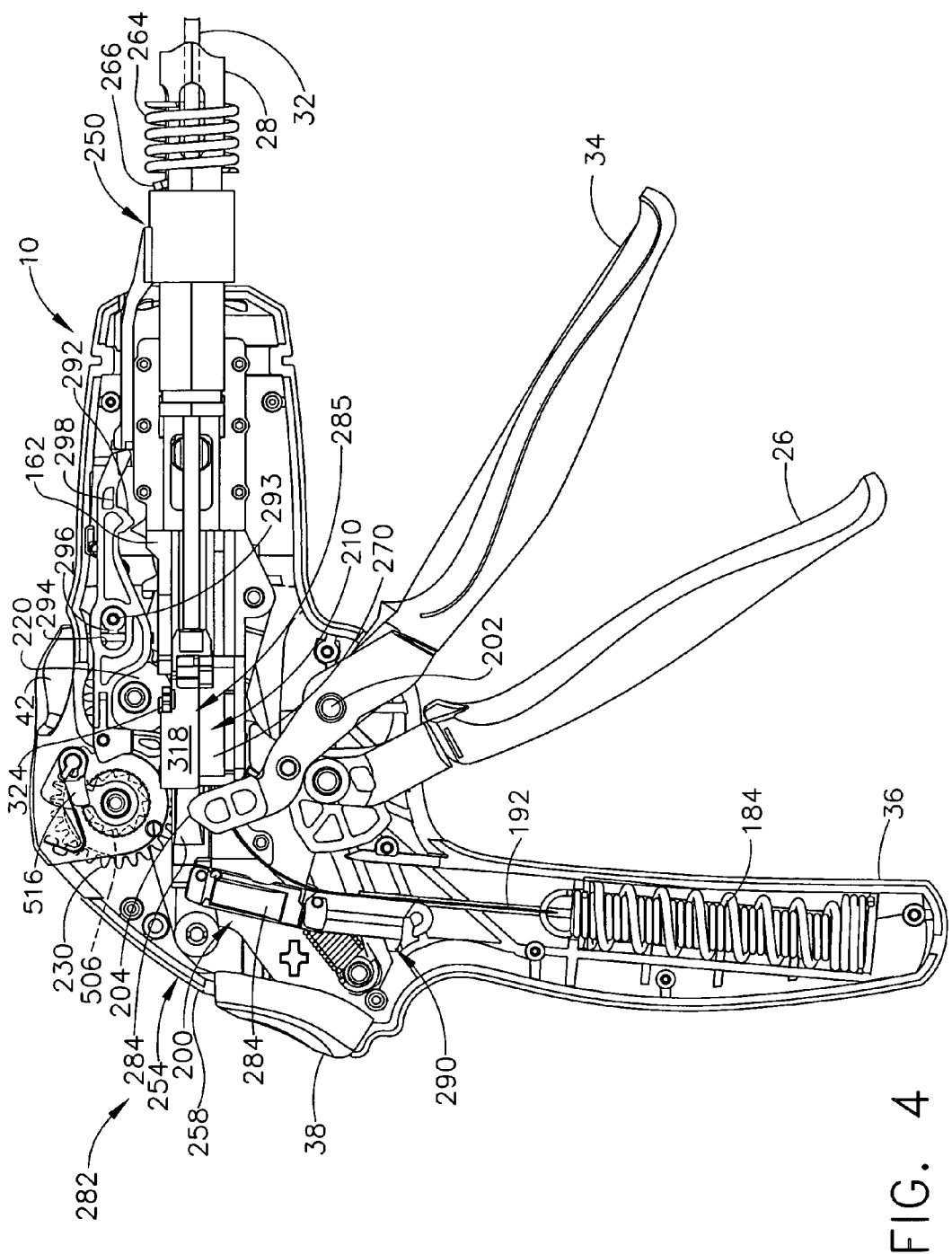
FIG. 4 is right side view of the surgical stapling and severing instrument of FIG. 1 with a right half shell and outer portions of the implement portion removed to expose the closure and firing mechanisms in an initial state.
Figure 5:
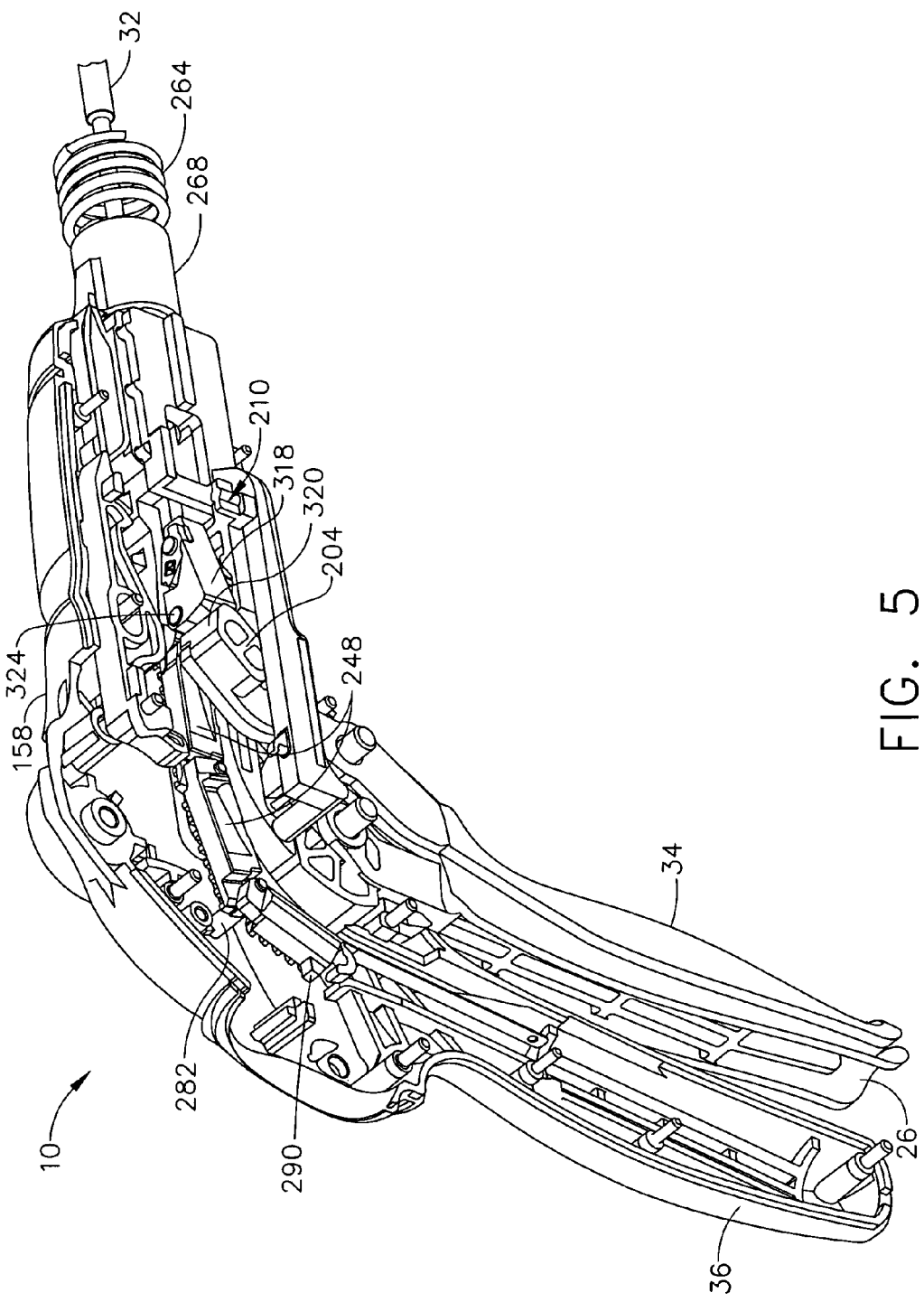
FIG. 5 is a right aft perspective view of the partially disassembled surgical stapling and severing instrument of FIG. 4 with a closure mechanism closed and clamped and the side pawl firing mechanism completing a first stroke and with a manual retraction mechanism removed to expose a distal link of the linked rack that triggers automatic retraction of the firing mechanism.

In FIGS. 3-5, an anti-backup mechanism 250 prevents the combination tension/compression spring 184 from retracting the linked rack 200 between firing strokes. A coupling slide tube 131 abuts the first link 196a and connects to the firing rod 32 to communicate the firing motion. The firing rod 32 extends proximally out of a proximal end of the frame 28 and through a through hole 408 of an anti-backup plate 266. The through hole 408 is sized to slidingly receive the firing rod 32 when perpendicularly aligned but to bind when tipped. A lower tab attachment 271 extends proximally from a lower lip of the proximal end of the frame 28, extending through an aperture 269 on a lower edge of the anti-backup plate 266. This lower tab attachment 271 draws the lower portion of the anti-backup plate 266 proximate to the frame 28 so that the anti-backup plate 266 is perpendicular when the firing rod 32 is distally advanced and allowed to tip top aft into a binding state when the firing rod 32 attempts to retract. An anti-backup compression spring 264 is distally constrained by the proximal end of the frame 28 and proximally abutts a top portion of the anti-backup plate 266, biasing the anti-backup plate 266 to a locking state.

Opposing the spring bias, an anti-backup cam tube 268 slidingly encompasses the coupling slide tube 131 and abuts the anti-backup plate 266. A proximally projecting anti-backup yoke 256 attached to the anti-backup cam tube 268 extends overtop of the closure yoke 162.

Linked Rack Triggered Automatic Retraction.

In FIGS. 1-5, a link triggered automatic retraction mechanism 289 is incorporated into the surgical stapling and severing instrument 10 to cause knife retraction at the end of full firing travel. To that end, the distal link 196d includes a tang 290 that projects upwardly when the distal link 196d is advanced into rack channel 291 formed in the closure yoke 162. This tang 290 is aligned to activate a bottom proximal cam 292 on an anti-backup release lever 248 (FIG. 40). Structures formed in the right and left half shells 156, 158 constrain movement of the anti-backup release lever 248. A pin receptacle 296 and circular pin 293, formed respectively between right and left half shells 156, 158, is received through a longitudinally elongate aperture 294 formed in the anti-backup release lever 248 distal to the bottom proximal cam 292, thus allowing longitudinal translation as well as rotation about the circular pin 293. In the right half shell 156, a proximally open channel 295 includes a proximal horizontal portion 295a that communicates with an upwardly and distally angled portion 295b that receives a rightward aft pin 297 (FIG. 39) near the proximal end of the anti-backup release lever 248, thus imparting an upward rotation as the anti-backup release lever 248 reaches the distal most portion of its translation. A blocking structure 333, formed in the right half shell 156 proximal to the anti-backup release lever 248, prevents proximal movement thereof once assembled to maintain rightward aft pin 297 in the proximally open channel 295.

A distal end 254 of the anti-backup release lever 248 thus is urged distally and downwardly, causing a rightward front pin 298 to drop into distally open step structure 299 formed in the right half shell 156, which is urged into this engagement by a compression spring 300 hooked to a leftward hook 301 on the anti-backup release lever 248 between the rightward front pin 298 and the longitudinally elongate aperture 294. The other end of the compression spring 300 is attached to a hook 302 formed in the right half shell 156 in a more proximal and lower position just above the closure yoke 162. The compression spring 300 thus pulls the distal end 254 of the anti-backup release lever 248 down and aft, which results in the rightward front pin 298 locking into the distally open step structure 299 when distally advanced.

Once tripped, the anti-backup release lever 248 remains forward holding the anti-backup plate 266 perpendicularly, thus allowing the linked rack 200 to be retracted. When the closure yoke 162 is subsequently retracted when unclamping the end effector 12, an upwardly projecting reset tang 303 on the closure yoke 162 contacts a bottom distal cam 305 of the anti-backup release lever 248, lifting the rightward front pin 298 out of the distally open step structure 299 so that the anti-backup compression spring 264 can proximally push the anti-backup cam tube 268 and the anti-backup release lever 248 to their retracted positions.

Side Pawl Firing Mechanism Incorporating EAP Lockout Mechanism.

Figure 6:
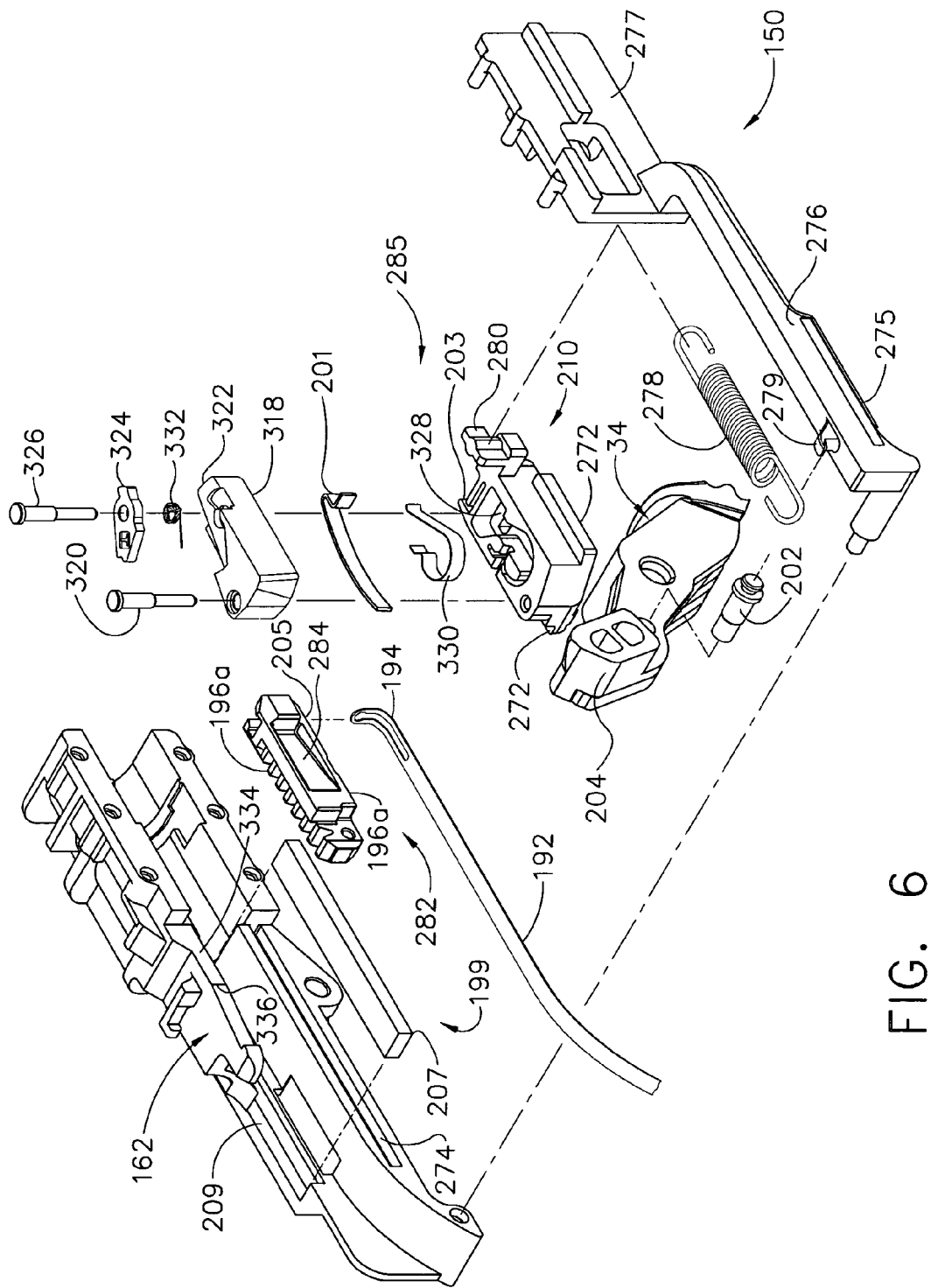
FIG. 6 is a detail right aft perspective view of a linked rack firing mechanism formed from the disassembled closure yoke assembly and the firing side pawl mechanism with an EAP firing lockout of FIG. 3.
Figure 7:
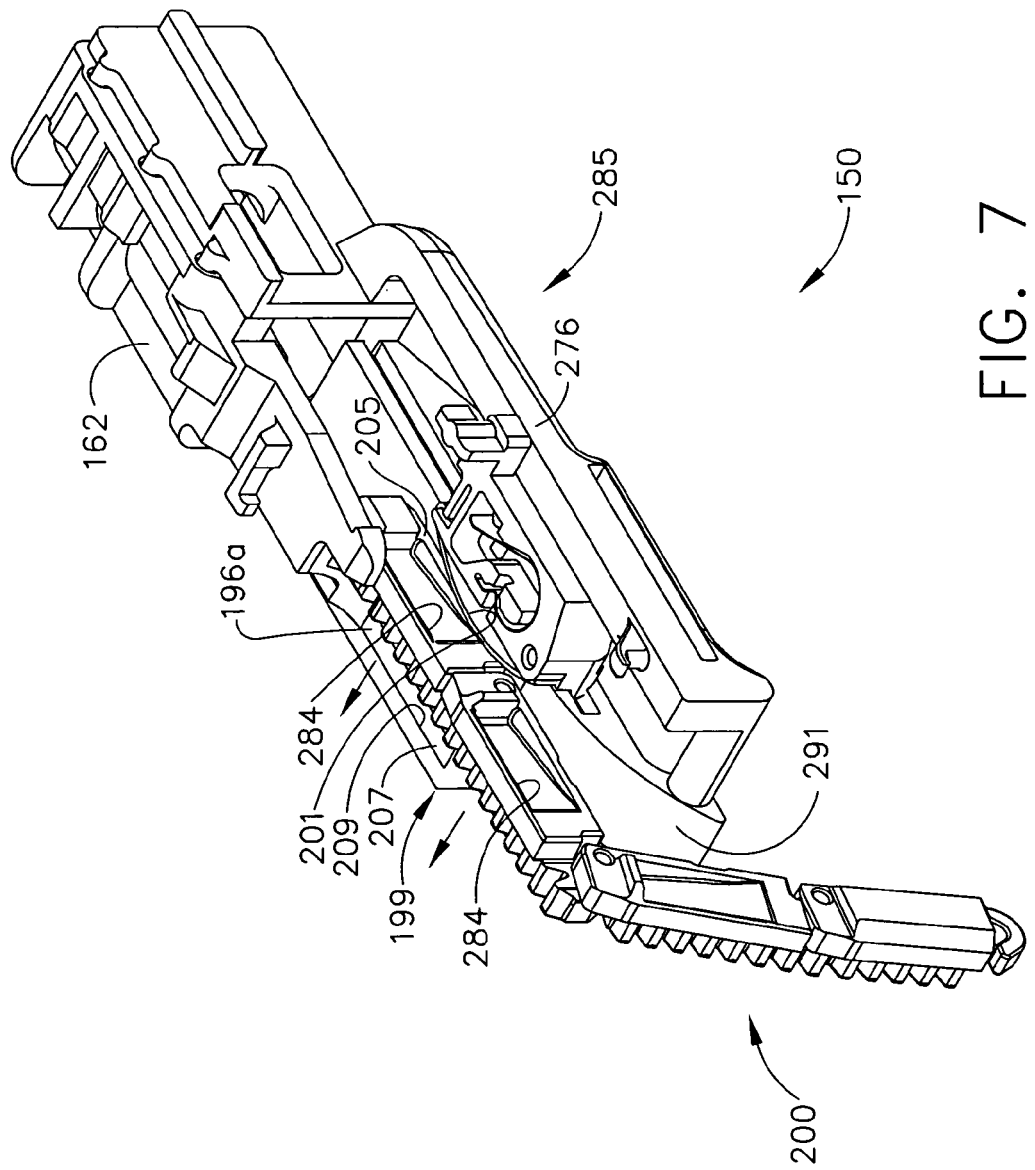
FIG. 7 is a right aft perspective view of the linked rack firing mechanism with a proximally retracted linked rack, closure yoke, closure yoke rail, and pawl slide of a side pawl assembly incorporating an EAP lockout mechanism depicted as disengaged (inactivated) electrically from the linked rack of the surgical stapling and severing instrument of FIG. 1.
Figure 8:
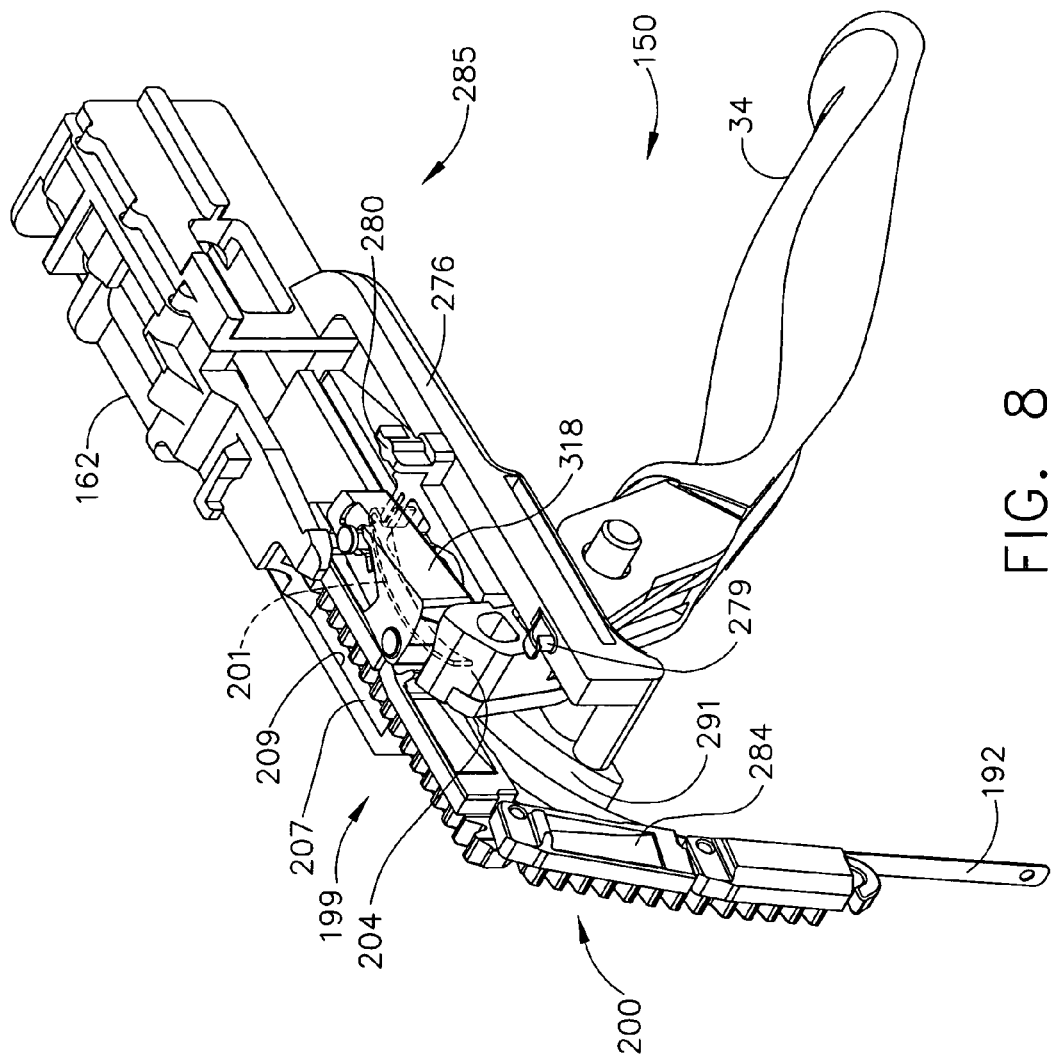
FIG. 8 is a right aft perspective view of the linked rack firing mechanism including a portion of the side pawl assembly of FIG. 7 with the addition of a firing trigger and pawl block with a bumper spring shown in phantom.
Figure 9:
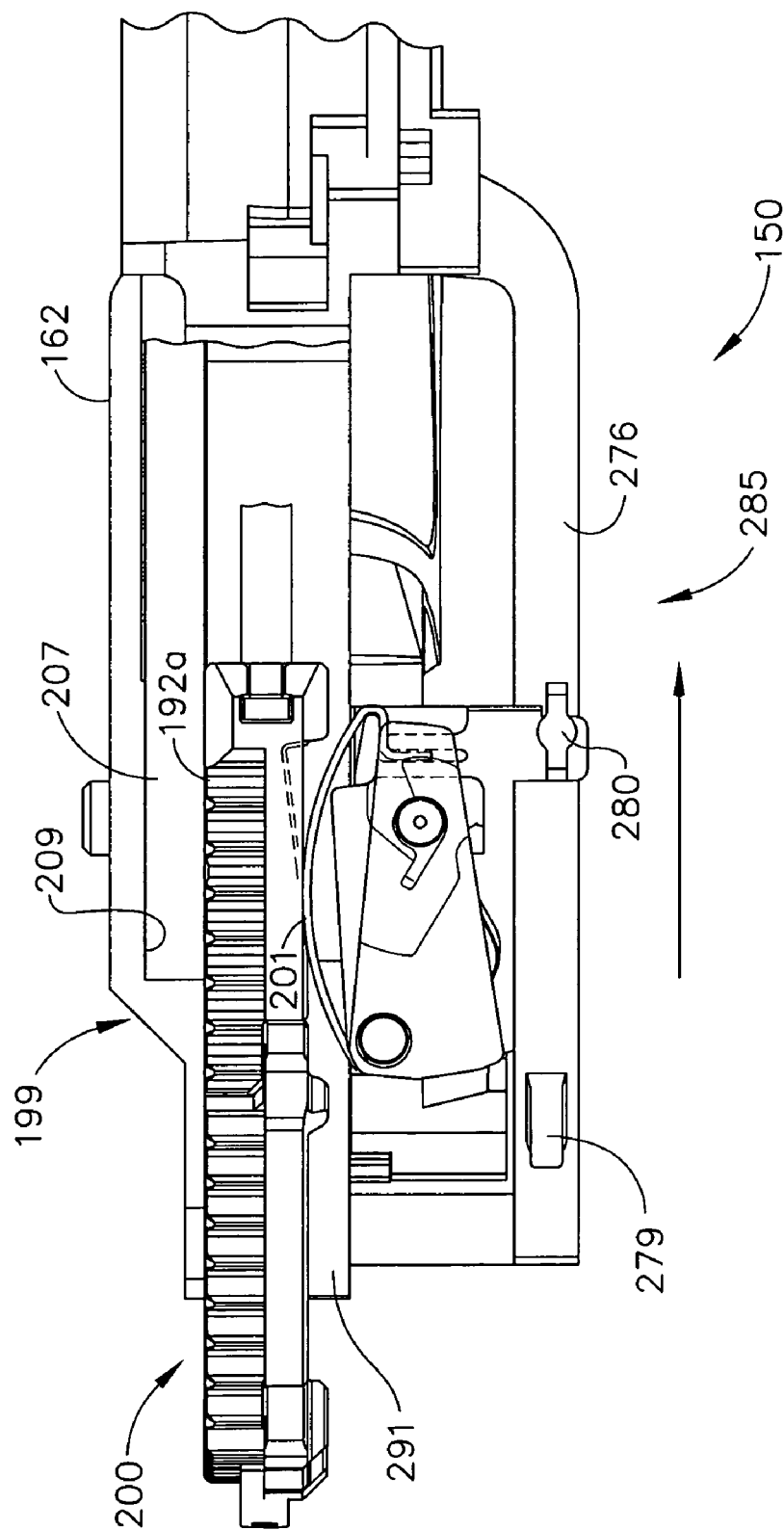
FIG. 9 is a top view of the linked rack firing mechanism including a portion of the side pawl assembly of FIG. 8 with the further addition of a kick-out block on the pawl block.
Figure 10:
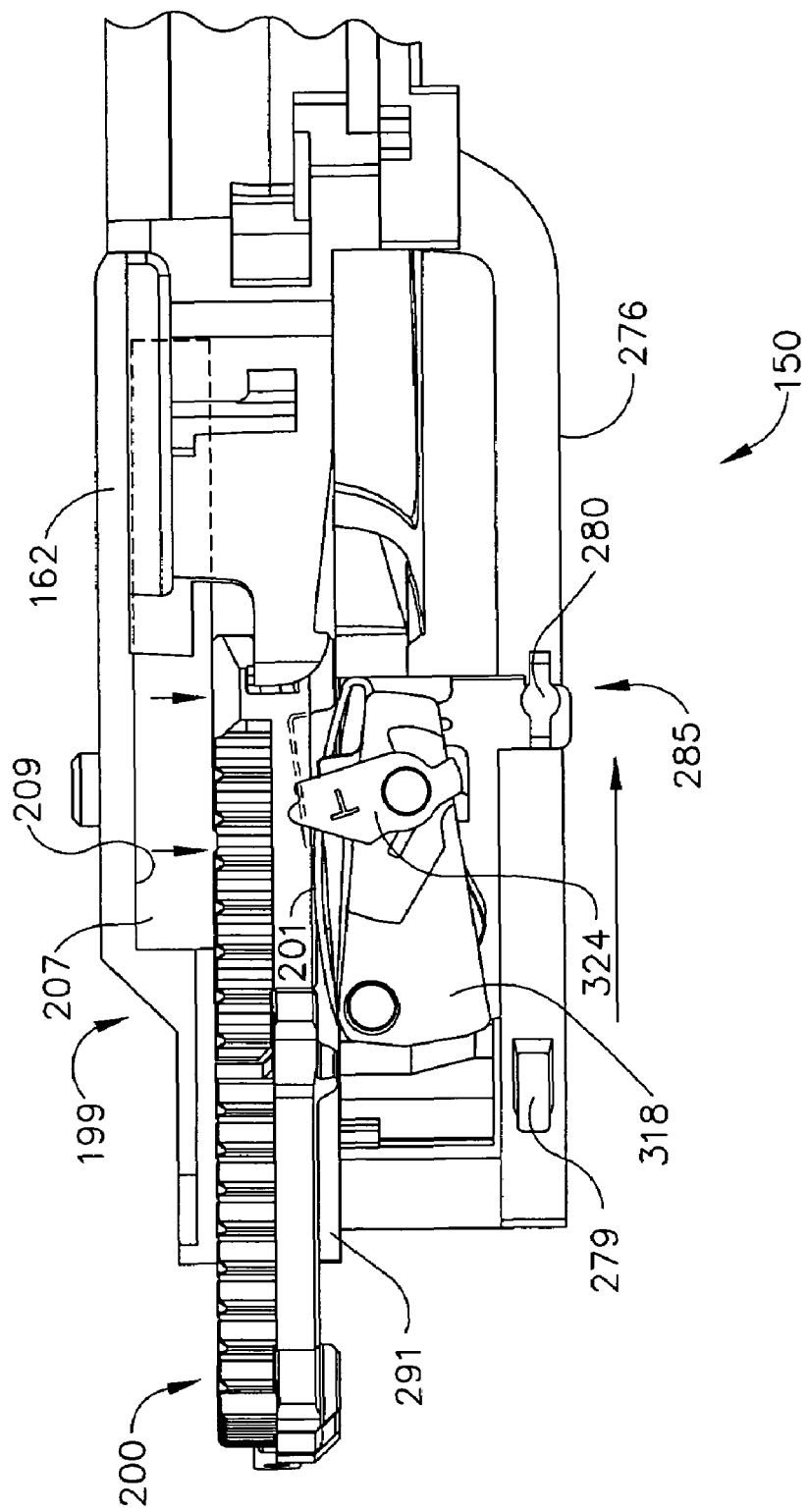
FIG. 10 is a top view of the linked rack firing mechanism of FIG. 9 with the EAP lockout mechanism activated, shifting the linked rack to the right into engagement with the pawl block and kick-out block.
Figure 11:
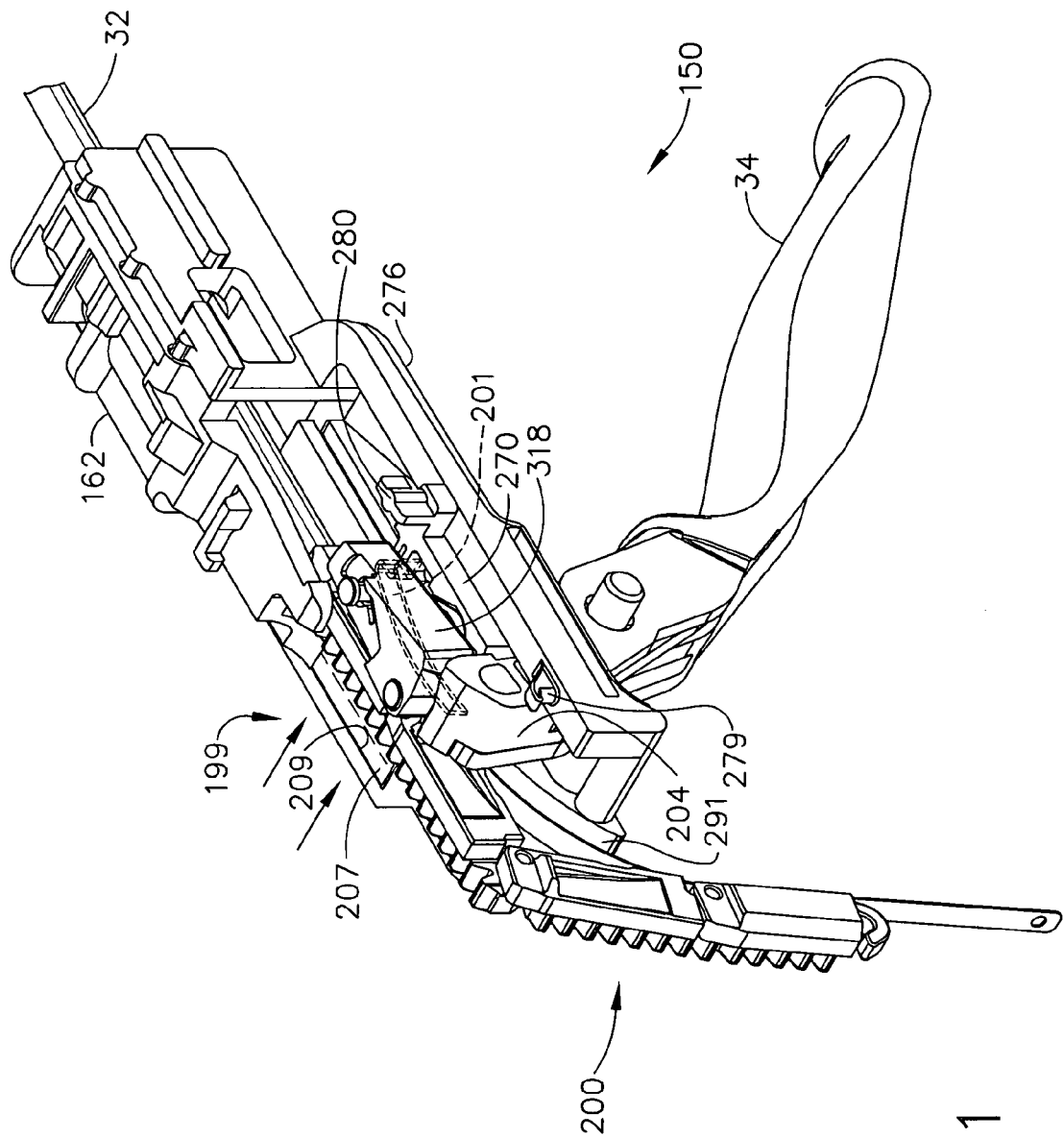
FIG. 11 is a right aft perspective view of the linked rack firing mechanism including the side pawl assembly, linked rack, closure yoke and rail, and firing trigger with the EAP lockout mechanism activated enabling firing.
Figure 12:
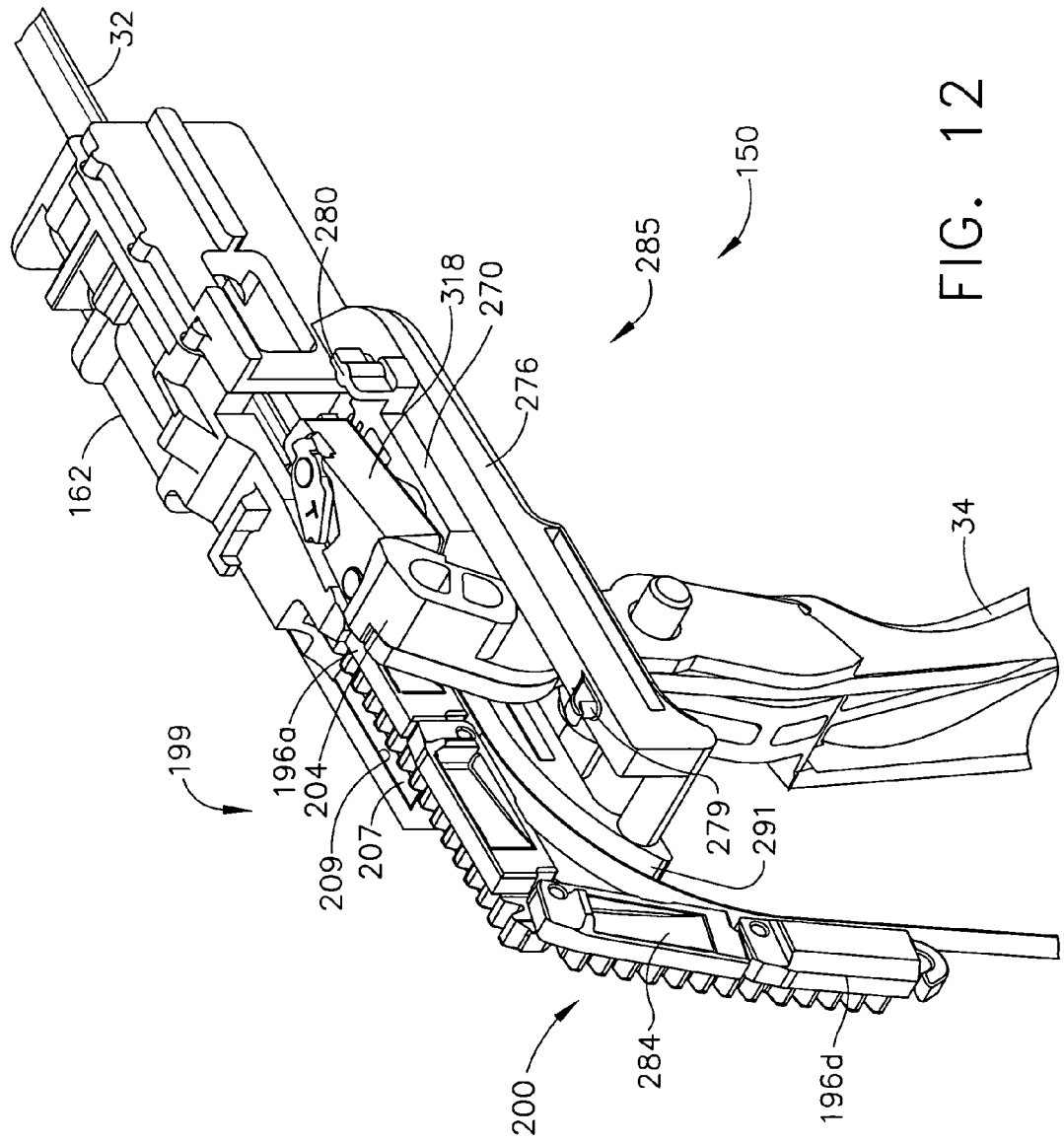
FIG. 12 is a right aft perspective view of the linked rack firing mechanism of FIG. 11 after a firing stroke with the EAP lockout mechanism inactivated, preventing advancement of the linked rack.

The handle 20, especially the linked rack firing mechanism 150, is described in greater detail in the afore-mentioned U.S. patent application Ser. No. 11/052,387 already incorporated by reference, such as depictions of a side pawl assembly intermittently driving a linked rack. In FIG. 6, however, a side pawl assembly 285 is modified to include an EAP lockout mechanism 199. In particular, modifications to the linked rack firing mechanism 150, specifically the closure yoke 162, pawl slide (shuttle) 270, and link 196a-d, allow a bumper spring 201 distally gripped in a curved vertically open slot 203 in the pawl slide 270, extending a proximal bowed portion along the left side of the pawl slide 270. Each link 196a-d has a horizontal recess 205 along the bottom of its right side to present an uninterrupted contact surface to the bumper spring 201 to receive a leftward bias therefrom, moving the linked rack 200 out of engagement. An EAP block actuator 207 retained in a rightwardly open horizontal slot 209 in the closure yoke 162, when activiated against the right side of the links 196a-d, urges the linked rack 200 into close proximity to the pawl slide 270, compressing the bumper spring 201, thereby enabling firing.

It should be appreciated that a number of control circuitry features may thus be incorporated to prevent firing. For example, an enabling switch may be added to the handle 20. As another example, sensors in the end effector 12 may be included, such as presence or absence of an unspent staple cartridge, and presence of an appropriate amount of tissue clamped into the end effector, presence or absence of ancillary compounds or therapeutic features (e.g., a cauterizing, sterilizing, etc.).

Electroactive Polymers.

Electroactive polymers (EAPs) are a set of conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually a central wire core and a conductive outer sheath, which also serve to contain the ionic fluid that surrounds the fiber bundles. An example of a commercially available fiber EAP material is manufactured by Santa Fe Science and Technology, sold as PANION fiber and described in U.S. Pat. No. 6,667,825, which is hereby incorporated by reference in its entirety.

The other type is a laminate structure. It consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is available from Artificial Muscle Inc, a division of SRI Laboratories. Plate EAP material is also available from EAMEX of Japan and referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. It may also be adhered to either side of a flexible plate. When one side of the flexible plate EAP is energized it would expand, flexing the plate in the opposite direction. This allows the plate to be flexed either direction depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of the EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30%, utilizing much higher voltages. It should be appreciated, however, that these performance ranges are not determinative.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers therebetween to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap, and then through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

Firing, Manual Retraction And Automatic Retraction.

With particular reference to FIGS. 2-5, the firing trigger 34 pivots about a firing trigger pin 202 that is connected to the housing 154. A firing actuator, depicted as an upper portion 204 of the firing trigger 34, moves distally about the firing trigger pin 202 as the firing trigger 34 is depressed toward pistol grip 36, stretching a proximally placed firing trigger tension spring 206 (FIG. 3) proximally connected between the upper portion 204 of the firing trigger 34 and the housing 154. The upper portion 204 of the firing trigger 34 engages the linked rack 200 during each firing trigger depression by a spring-biased side pawl mechanism 210 that also disengages when the firing trigger 34 is released.

In particular, a ramped right-side track 282 formed by a proximally and rightwardly facing beveled surface 284 in each of the links 196a-1196d is engaged by a side pawl assembly 285. In particular, the pawl slide (shuttle) 270 (FIGS. 3, 6) has right and left lower guides 272 that slide respectively in a left track 274 (FIGS. 3, 6) formed in the closure yoke 162 below the rack channel 291 and a right track 275 in a closure yoke rail 276 that parallels rack channel 291 and is attached to a rack channel cover 277 that closes a rightwardly open portion of the rack channel 291 in the closure yoke 162 that is distal to the travel of the pawl slide 270. In FIGS. 3, 6, a compression spring 278 is attached between a hook 279 on a top proximal position on the closure yoke rail 276 and a hook 280 on a distal right side of the pawl slide 270, which keeps the pawl slide 270 drawn proximally into contact with the upper portion 204 of the firing trigger 34. The other depictions omit the compression spring 278 for clarity.

With particular reference to FIG. 6, a pawl block 318 sits on the pawl slide 270 pivoting about a vertical aft pin 320 that passes through a left proximal corner of pawl block 318 and pawl slide 270. A kick-out block recess 322 is formed on a distal portion of a top surface of the block 318 to receive a kick-out block 324 pivotally pinned therein by a vertical pin 326 whose bottom tip extends into a pawl spring recess 328 on a top surface of the pawl slide 270. A pawl spring 330 in the pawl spring recess 328 extends to the right of the vertical front pin 326, urging the pawl block 318 to rotate counterclockwise when viewed from above into engagement with the ramped right-side track 282. A small coil spring 332 in the kick-out block recess 322 urges the kick-out block 324 to rotate clockwise when viewed from above, its proximal end urged into contact with a contoured lip 334 formed in the closure yoke 162 above the rack channel 291.

The stronger mechanical advantage of the pawl spring 330 over the small coil spring 332 means that the pawl block 318 tends toward engagement with the kick-out block 324 rotated clockwise. In FIG. 5, as the firing trigger 34 is fully depressed and begins to release, the kick-out block 324 encounters a ridge 336 in the contoured lip 334 as the pawl slide 270 retracts, forcing the kick-out block 324 to rotate clockwise when viewed from above and thereby kicking out the pawl block 318 from engagement with the linked rack 200. The shape of the kick-out block recess 322 stops the clockwise rotation of the kick-out block 324 to a perpendicular orientation to the contoured lip 334, maintaining this disengagement during the full retraction and thereby eliminating a ratcheting noise.

In FIG. 3, the surgical stapling and severing instrument 10 includes a manual retraction mechanism 500 that provides firing position indication, manual release of the firing mechanism and manual retraction. In particular, a gear mechanism 502 also functions to visually indicate progress of firing travel and to manually retract the knife. A front idler gear 220 engages a toothed upper, left surface 222 of the linked rack 200. The front idler gear 220 also engages an aft idler gear 230 having a smaller right-side ratchet gear 231. Both the front idler gear 220 and aft idler gear 230 are rotatably connected to the handle housing 154 respectively on front idler axle 232 and aft idler axle 234. Each end of the aft axle 232 extends through the respective right and left housing half shells 156, 158 and is attached to the left and right indicator gauge wheels 40, 41. Since the aft axle 234 is free spinning in the handle housing 154 and has a keyed engagement to the aft gear 230, the indicator gauge wheels 40, 41 rotate with the aft gear 230. The gear relationship between the linked rack 200, idler gear 220 and aft gear 230 may be advantageously selected so that the toothed upper surface 222 has tooth dimensions that are suitably strong and so that the aft gear 230 makes no more than one revolution during the full firing travel of the linked transmission firing mechanism 150.

The smaller right-side ratchet gear 231 of the aft idler gear 230 extends into a hub 506 of the manual retraction lever 24, specifically aligned with a vertical longitudinally-aligned slot 508 (FIG. 42) bisecting the hub 506. A lateral through hole 510 of the hub 506 communicates with an upper recess 512. A front portion 514 is shaped to receive a proximally directed locking pawl 516 that pivots about a rightward lateral pin 518 formed in a distal end of the upper recess 512. An aft portion 520 is shaped to receive an L-shaped spring tab 522 that urges the locking pawl 516 downward into engagement with the right-side smaller ratchet gear 231. A hold-up structure 524 projects from the right half shell 156 into the upper recess 512, holding up the locking pawl 516 from engaging the smaller right-side ratchet gear 231 when the manual retraction lever 42 is down. A coil spring 525 (FIG. 3) urges the manual retraction lever 42 down. As the manual retraction lever 42 is raised, the locking pawl 516 rotates clockwise, is no longer held up by the hold-up structure 524 and engages the smaller right-side ratcheting gear 231, rotating the aft idler gear 230 clockwise when viewed from the left. Thus, the forward idler gear 220 responds counterclockwise, retracting the linked rack 200. In addition, a rightward curved ridge 530 projects out from the hub 506, sized to contact and distally move the anti-backup release lever 248 to release the anti-backup mechanism 250 as the manual retraction lever 42 is rotated.

Operation of the EAP Blocking Lockout Mechanism.

In FIGS. 7-12, the side pawl assembly 285 is depicted in operation performing locking out of firing. In particular, in FIGS. 7-9, the pawl slide 270 is laterally constrained by being longitudinally guided between the closure yoke 162 and the closure yoke rail 276. The bumper spring 201 extends laterally to the left of the pawl slide 270 and the horizontal recess 205 of an adjacent link 196a of the linked rack 200, urging the linked rack to the left across the rack channel 291 formed in the closure yoke 162. The EAP block actuator 207 is laterally contracted in a deactivated state, confined within the rightwardly open horizontal slot 209 in the closure yoke. Thus, with the firing trigger 34 drawn from its relaxed position (FIG. 8) to its depressed position (FIG. 12), the top portion 204 of the firing trigger 34 advances the pawl block 318 without engaging the proximally and rightwardly facing beveled surface 284 of the link 196a. Thus, no force is imparted to the linked rack 200 that would have to be blocked downstream in the event of an undesirable firing condition.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

It will be appreciated that the terms "proximal" and "distal" are used herein with reference to a clinician gripping a handle of an instrument. Thus, the end effector 12 is distal with respect to the more proximal handle 20. Analogous terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The present invention is being discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

Applications consistent with the present invention may include single firing stroke instruments as well as those with a solid firing rack rather than a linked rack.

The linked rack 200 serves as a proximal engaging portion of a firing member that actuates the implement portion 22. It should be appreciated that a frictional engagement may be used instead of a spring-biased side pawl assembly 285, such as described in co-pending and commonly-owned U.S. patent application Ser. No. 10/673,662 to Jeffrey S. Swayze, et al., entitled "SURGICAL STAPLING INSTRUMENT HAVING MULTISTROKE FIRING INCORPORATING A TRACTION-BIASED RACHETING MECHANISM.", the disclosure of which is hereby incorporated by reference in its entirety.

In addition, the orientation of the side pawl assembly 285 to a linked rack 200 to its left is illustrative. It should be appreciated that a linked or solid rack may be oriented above, below, or to the right of a selectively engaging member coupled to a firing trigger (e.g., spring biased pawl, traction biased member).

In the above-described versions, a side pawl is spring biased into engagement with the rack 200 but held out of engagement during proximal movement when the firing trigger is released. A spring biases the pawl slide to avoid engagement unless overcome by the EAP lockout actuator. It should also be appreciated that applications consistent with the present invention may include an EAP lockout actuator that biases a pawl into engagement with a rack of a firing mechanism. Thus, a pawl may be biased out of engagement. A sensor coupled to a firing trigger enables an EAP lockout actuator, when the firing trigger is sensed, from being depressed and not released. The EAP lockout actuator is activated (optionally with other preconditions met) urging the pawl into engagement with the rack.

In the above-described versions, a rack and pawl engagement is advantageously described as providing a strong transfer of firing motion from a firing trigger to a firing bar. It should be appreciated that applications consistent with the present application may include a frictional engagement between a proximal portion of a firing member and a firing actuator such as a firing trigger. An EAP lockout actuator may prevent binding contact by effecting spacing or preventing a binding deflection (e.g., screen door damper lock).

As another example, the lockout mechanism may comprise an EAP actuator positioned on an opposite side of the pawl slide from the rack to push the pawl slide toward a rack. Further, this EAP actuator may be attached to the pawl slide or to a relatively stationary part of the handle adjacent to the pawl slide.

As yet another example, a bias of the lockout mechanism urging the proximal engaging portion of the firing member (e.g., rack) away from the engagement mechanism (e.g., pawl/pawl slide) may comprise a resilient strip of material affixed to an inner surface of the proximal engaging portion of the firing member and/or the engagement mechanism.

What is claimed is:

1. A surgical instrument, comprising:
   an implement portion actuated by a distally moving firing member having a proximal engaging portion;
   a firing actuator proximate to and aligned with the proximal engaging portion of the firing member, the firing actuator operatively configured to longitudinally reciprocate;
   an engagement mechanism operatively configured to couple distal movement of the firing actuator into the proximal engaging portion of the firing member; and
   a lockout mechanism comprising:
      a disengaging biasing member uncoupling the engagement mechanism, and
      an electrical actuator opposingly positioned to overcome the disengaging biasing member when activated.

2. The surgical instrument of claim 1, wherein the electrical actuator of the lockout mechanism comprises an electroactive polymer actuator.

3. The surgical instrument of claim 1, wherein the proximal engaging portion of the firing member comprises a rack.

4. The surgical instrument of claim 3, wherein the proximal engaging portion of the firing member comprises a linked rack.

5. The surgical instrument of claim 3, wherein the engagement mechanism includes a pawl biased into engagement with the rack during distal movement of the pawl.

6. The surgical instrument of claim 1, further comprising a channel that constrains a selected one of the firing member and the engagement mechanism for reciprocating firing movement with allowance for selective transverse movement toward and away from the other of the firing member and the engagement member.

7. The surgical instrument of claim 6, wherein the engagement mechanism comprises a pawl slide supporting a pawl, the proximal engaging portion of the firing member comprising a rack.

8. The surgical instrument of claim 7, wherein the lockout mechanism further comprises a spring attached to the pawl slide and in sliding contact with the rack.

9. The surgical instrument of claim 6, wherein the electrical actuator is positioned on an opposite side of the proximal engaging portion of the firing member than the engagement mechanism and operatively configured when activated to urge the proximal engaging portion toward the engagement mechanism.

10. The surgical instrument of claim 1, wherein the firing actuator comprises a single firing stroke trigger.

11. The surgical instrument of claim 1, wherein the firing actuator comprises a multiple firing stroke trigger.

12. The surgical instrument of claim 1, wherein the firing actuator comprises a multiple firing stroke trigger.

13. The surgical instrument of claim 1, further comprising a closure trigger operatively configured to close the opposing jaws to clamp tissue.

14. A surgical instrument, comprising:
   an end effector comprising pivotally attached opposing jaws and a staple cartridge contained in one of the opposing jaws;
   a distally moving firing bar member comprising a distal portion operably configured to actuate the staple cartridge and to sever tissue clamped in the opposing jaws;
   a rack attached proximally to the firing bar member;
   a reciprocating firing actuator proximate to and aligned with the rack;
   an engagement mechanism operatively configured to couple distal movement of the firing actuator into the rack;
   a lockout mechanism comprising:
      a disengaging biasing member uncoupling the engagement mechanism from the rack, and
      an electrical actuator opposingly positioned to overcome the disengaging biasing member when activated.

15. The surgical instrument of claim 14, wherein the electrical actuator of the lockout mechanism comprises an electroactive polymer actuator.

16. The surgical instrument of claim 14, wherein the proximal engaging portion of the firing member comprises a linked rack.

17. The surgical instrument of claim 14, wherein the engagement mechanism includes a pawl biased into engagement with the rack during distal movement of the pawl.

18. The surgical instrument of claim 14, further comprising a rack guide that constrains the rack and the engagement mechanism for reciprocating firing movement with allowance for selective transverse movement toward and away from each other.

19. The surgical instrument of claim 18, wherein the engagement mechanism comprises a pawl slide supporting a pawl.

20. The surgical instrument of claim 19, wherein the lockout mechanism further comprises a spring attached to the pawl slide and in sliding contact with the rack.

21. The surgical instrument of claim 18, wherein the electrical actuator comprises an electroactive polymer actuator positioned on adjacent to a selected one of the proximal engaging portion of the firing member and than the engagement mechanism opposite to the other and operatively configured when activated to urge the selected one of the proximal engaging portion and the engagement mechanism toward the other.

* * * * *